(12) United States Patent
Greenberg et al.

(10) Patent No.: US 9,283,085 B2
(45) Date of Patent: Mar. 15, 2016

(54) INTERVERTEBRAL DISC PROSTHESIS AND METHOD

(71) Applicant: Blackstone Medical, Inc., Lewisville, TX (US)

(72) Inventors: Daniel Greenberg, Ramsey, NJ (US); James Klein, Dallas, TX (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

(21) Appl. No.: 14/589,661

(22) Filed: Jan. 5, 2015

(65) Prior Publication Data

US 2015/0119991 A1    Apr. 30, 2015

Related U.S. Application Data

(62) Division of application No. 13/362,932, filed on Jan. 31, 2012.

(51) Int. Cl.
*A61F 2/44* (2006.01)
*A61F 2/46* (2006.01)
(Continued)

(52) U.S. Cl.
CPC . *A61F 2/44* (2013.01); *A61F 2/442* (2013.01); *A61F 2/447* (2013.01); *A61F 2/4611* (2013.01); *A61F 2002/2835* (2013.01); *A61F 2002/3008* (2013.01); *A61F 2002/30092* (2013.01); *A61F 2002/30354* (2013.01); *A61F 2002/30365* (2013.01); *A61F 2002/30367* (2013.01); *A61F 2002/30484* (2013.01); *A61F 2002/30509* (2013.01); *A61F 2002/30578* (2013.01); *A61F 2002/30579* (2013.01); *A61F 2002/30626* (2013.01); *A61F 2002/30632* (2013.01); *A61F 2002/30782* (2013.01); *A61F 2002/30828* (2013.01); *A61F 2002/4475* (2013.01); *A61F 2002/4687* (2013.01); *A61F 2310/00023* (2013.01)

(58) Field of Classification Search
CPC ..... A61F 2/447; A61F 2/4455; A61F 2/4611; A61F 2/44; A61F 2/442
See application file for complete search history.

(56) References Cited

U.S. PATENT DOCUMENTS

| 3,426,364 A | 2/1969 | Lumb |
| 4,401,112 A | 8/1983 | Rezaian |
| 4,657,550 A | 4/1987 | Daher |

(Continued)

FOREIGN PATENT DOCUMENTS

| EP | 2047825 A1 | 4/2009 |
| FR | 2737656 A1 | 2/1997 |

(Continued)

OTHER PUBLICATIONS

Extended European Search Report, EP Appl. No. 13743564.0, dated Sep. 2, 2015, 7 pages.

(Continued)

*Primary Examiner* — Christian Sevilla
(74) *Attorney, Agent, or Firm* — Baker & McKenzie LLP

(57) ABSTRACT

The present disclosure generally relates to an intervertebral disc prosthesis for partially or totally replacing an organic intervertebral disc. The disc prosthesis includes an interbody device, a face plate and a pair of locking mechanisms for achieving dual fixation in the cephalad and caudal direction. Methods according to the present disclosure achieve such dual fixation in a single fixation step.

5 Claims, 8 Drawing Sheets

(51) Int. Cl.
*A61F 2/28* (2006.01)
*A61F 2/30* (2006.01)

(56) References Cited

U.S. PATENT DOCUMENTS

| | | | |
|---|---|---|---|
| 4,759,769 A | 7/1988 | Hedman et al. | |
| 5,059,193 A | 10/1991 | Kuslich | |
| 5,258,031 A | 11/1993 | Salib et al. | |
| 5,556,431 A | 9/1996 | Buttner-Janz | |
| 5,683,394 A | 11/1997 | Rinner | |
| 5,713,899 A | 2/1998 | Marnay et al. | |
| 5,776,198 A | 7/1998 | Rabbe et al. | |
| 5,800,550 A * | 9/1998 | Sertich | A61F 2/447 606/247 |
| 5,888,228 A | 3/1999 | Knothe et al. | |
| 5,895,428 A | 4/1999 | Berry | |
| 6,066,175 A | 5/2000 | Henderson et al. | |
| 6,090,143 A | 7/2000 | Meriwether et al. | |
| 6,093,205 A | 7/2000 | McLeod et al. | |
| 6,102,950 A * | 8/2000 | Vaccaro | A61F 2/447 606/247 |
| 6,156,037 A | 12/2000 | LeHuec et al. | |
| 6,179,873 B1 | 1/2001 | Zientek | |
| 6,235,059 B1 | 5/2001 | Benezech et al. | |
| 6,447,546 B1 | 9/2002 | Bramlet et al. | |
| 6,629,998 B1 * | 10/2003 | Lin | A61F 2/447 623/17.11 |
| 6,770,096 B2 | 8/2004 | Bolger et al. | |
| 6,972,019 B2 | 12/2005 | Michelson | |
| 7,135,043 B2 | 11/2006 | Nakahara et al. | |
| 7,235,105 B2 | 6/2007 | Jackson | |
| 7,238,203 B2 | 7/2007 | Bagga et al. | |
| 7,442,209 B2 | 10/2008 | Michelson | |
| 7,594,932 B2 | 9/2009 | Aferzon et al. | |
| 7,794,502 B2 | 9/2010 | Michelson | |
| 8,167,950 B2 | 5/2012 | Aferzon et al. | |
| 8,920,505 B2 | 12/2014 | Aferzon et al. | |
| 2001/0020185 A1 * | 9/2001 | Ray | A61F 2/446 623/17.11 |
| 2002/0004683 A1 | 1/2002 | Michelson | |
| 2002/0055737 A1 * | 5/2002 | Lieberman | A61B 17/7032 606/247 |
| 2002/0055738 A1 | 5/2002 | Lieberman | |
| 2002/0107572 A1 * | 8/2002 | Foley | A61F 2/446 623/17.11 |
| 2003/0045877 A1 | 3/2003 | Yeh | |
| 2003/0125739 A1 * | 7/2003 | Bagga | A61F 2/442 606/247 |
| 2003/0176925 A1 | 9/2003 | Paponneau | |
| 2003/0187436 A1 * | 10/2003 | Bolger | A61B 17/0206 623/17.11 |
| 2003/0229348 A1 | 12/2003 | Sevrain | |
| 2004/0010254 A1 | 1/2004 | Cook et al. | |
| 2004/0034423 A1 | 2/2004 | Lyons et al. | |
| 2004/0049279 A1 * | 3/2004 | Sevrain | A61B 17/7059 623/17.13 |
| 2004/0073313 A1 | 4/2004 | Link et al. | |
| 2004/0111161 A1 | 6/2004 | Trieu | |
| 2004/0249461 A1 * | 12/2004 | Ferree | A61F 2/2846 623/17.11 |
| 2005/0060034 A1 | 3/2005 | Berry et al. | |
| 2005/0101960 A1 * | 5/2005 | Fiere | A61B 17/7059 623/17.11 |
| 2005/0165485 A1 | 7/2005 | Trieu | |
| 2005/0177245 A1 | 8/2005 | Leatherbury et al. | |
| 2005/0216081 A1 | 9/2005 | Taylor | |
| 2005/0222683 A1 | 10/2005 | Berry | |
| 2005/0283236 A1 | 12/2005 | Razian | |
| 2006/0074490 A1 | 4/2006 | Sweeney | |
| 2006/0095136 A1 * | 5/2006 | McLuen | A61F 2/4455 623/23.47 |
| 2006/0195100 A1 | 8/2006 | Kirschman | |
| 2006/0224241 A1 | 10/2006 | Butler et al. | |
| 2006/0282165 A1 | 12/2006 | Pisharodi | |
| 2007/0118225 A1 | 5/2007 | Hestad et al. | |
| 2007/0173936 A1 | 7/2007 | Hester et al. | |
| 2007/0191953 A1 | 8/2007 | Trieu | |
| 2007/0213820 A1 | 9/2007 | Magerl et al. | |
| 2007/0225806 A1 | 9/2007 | Squires et al. | |
| 2008/0033440 A1 * | 2/2008 | Moskowitz | A61B 17/0642 606/251 |
| 2008/0051890 A1 | 2/2008 | Waugh et al. | |
| 2008/0051900 A1 | 2/2008 | de Villiers et al. | |
| 2008/0177390 A1 | 7/2008 | Mitchell et al. | |
| 2008/0294260 A1 | 11/2008 | Gray | |
| 2008/0312698 A1 | 12/2008 | Bergeron et al. | |
| 2009/0105831 A1 | 4/2009 | Jones et al. | |
| 2009/0240333 A1 | 9/2009 | Trudeau et al. | |
| 2010/0057206 A1 | 3/2010 | Duffield et al. | |
| 2010/0131067 A1 | 5/2010 | Metcalf, Jr. et al. | |
| 2010/0137989 A1 | 6/2010 | Armstrong et al. | |
| 2010/0161057 A1 | 6/2010 | Berry et al. | |
| 2010/0204737 A1 | 8/2010 | Bae et al. | |
| 2010/0234958 A1 | 9/2010 | Linares | |
| 2011/0060415 A1 | 3/2011 | Bertholet et al. | |
| 2011/0190892 A1 | 8/2011 | Kirschman | |
| 2011/0208311 A1 | 8/2011 | Janowski | |
| 2011/0230971 A1 | 9/2011 | Donner et al. | |

FOREIGN PATENT DOCUMENTS

| | | |
|---|---|---|
| WO | 2010/071707 A1 | 6/2010 |
| WO | 2010/092893 A1 | 8/2010 |

OTHER PUBLICATIONS

Office Action, U.S. Appl. No. 13/362,932, dated Jan. 28, 2015, 15 pages.

International Search Report and Written Opinion, PCT/US2013/024052, dated Apr. 15, 2013, 9 pages.

\* cited by examiner

INTERVERTEBRAL DISC PROSTHESIS AND METHOD

PRIORITY

The present disclosure claims priority to and is a divisional application of U.S. patent application Ser. No. 13/362,932, entitled "Intervertebral Disc Prosthesis and Method" and filed Jan. 31, 2012, the entirety of which is hereby incorporated by reference.

TECHNICAL FIELD

The present disclosure generally relates to the field of orthopedics and spinal surgery, and more particularly, to intervertebral prosthetic devices for use in the total or partial replacement of a natural intervertebral disc, and related methods.

BACKGROUND

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are taken to ensure the proper spacing of the vertebrae formerly separated by the removed disc tissue.

Such corrective measures may include insertion of a disc prosthesis into the disc space. Surgical techniques for inserting intervertebral disc prostheses into the spinal column are high risk procedures given the proximity of the spinal cord to the surgical area. Accordingly, devices and methods for simplifying such procedures are desirable.

BRIEF SUMMARY

The present disclosure generally relates to an intervertebral disc prosthesis adapted for insertion into a space between adjacent vertebrae in the spinal column. In some embodiments, the disc prosthesis includes an interbody device, which cooperates with a face plate and associated fixation mechanisms to secure the interbody device in the disc space. The fixation mechanisms may take the form of tusks and/or screws, which engage endplates of the vertebrae adjacent to the disc space. Preferably, the face plate may be secured to the interbody device in such a way as to pivot relative to the interbody device and to thereby engage the fixation mechanism with the endplate(s). In some embodiments, a separate fixation mechanism may be used to engage the face plate to effect the desired rotation of the face plate. Related methods for inserting the disc prosthesis into the disc space are also described.

BRIEF DESCRIPTION OF THE DRAWINGS

Reference is now made to the following descriptions taken in conjunction with the accompanying drawings.

DETAILED DESCRIPTION

Various aspects of an intervertebral disc prosthesis and methods of using same according to the present disclosure are described. It is to be understood, however, that the following explanation is merely exemplary in describing the devices and methods of the present disclosure. Accordingly, several modifications, changes and substitutions are contemplated.

Figure 1A:
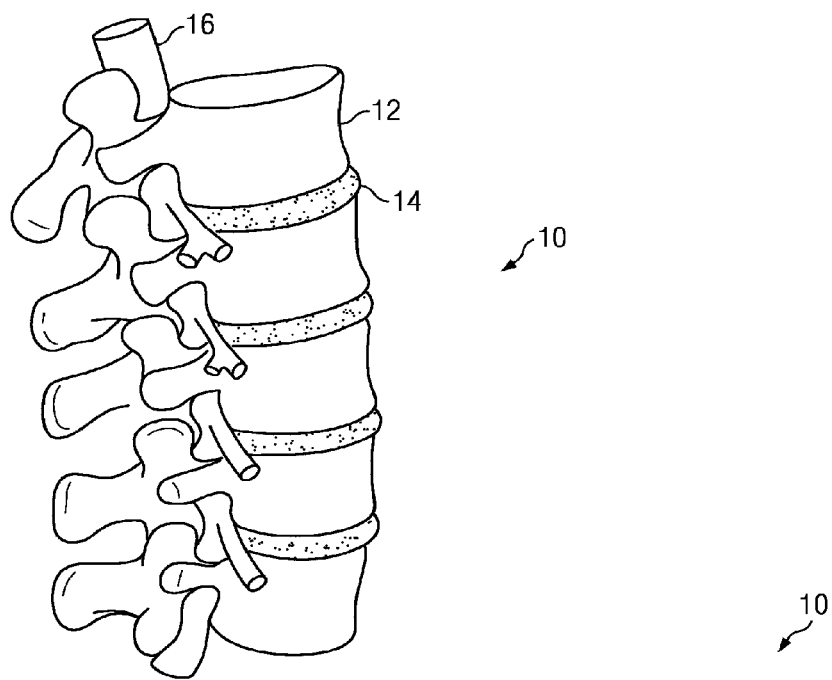
FIG. 1A illustrates a portion of a human spinal column.
Figure 1B:
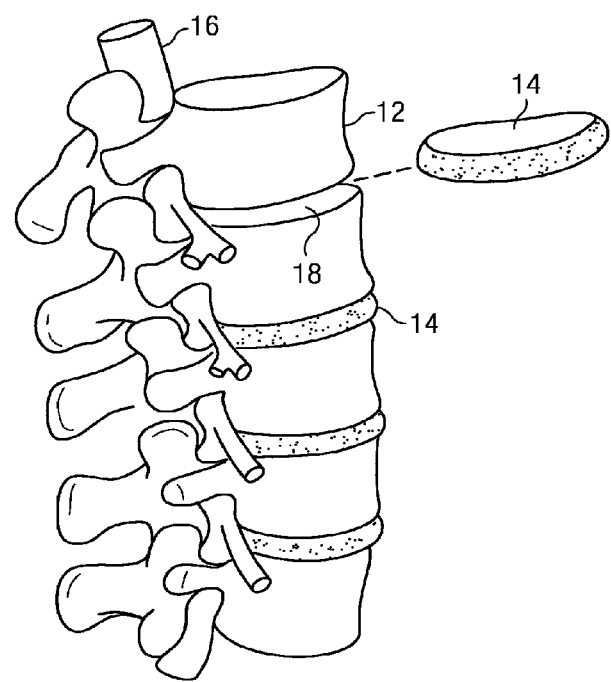
FIG. 1B illustrates a portion of a human spinal column with an intervertebral disc removed.

A portion of a human spinal column 10 is schematically illustrated in FIG. 1A and includes a series of vertebrae 12 intersected by a series of intervertebral discs 14. The vertebrae 12 generally encapsulate a spinal cord 16, which generally comprises nervous tissue and serves as the main pathway for information connecting the brain and peripheral nervous system. Referring to FIG. 1B, it sometimes becomes necessary to remove a diseased, or otherwise failing, intervertebral disc. Such procedures leave an intervertebral disc space 18 defined between adjacent vertebrae of the spinal column.

An intervertebral disc prosthesis 20 according to some embodiments of the present disclosure is illustrated in FIGS. 2-5. The prosthesis 20 is preferably used in the cervical and/or lumbar regions of the spinal column, however, other regions of use are contemplated as falling within the scope of the present disclosure. The disc prosthesis 20 includes an interbody device 22 and one or more fixation mechanisms 24 adapted for use with the interbody device. The disc prosthesis 20 further includes a face plate 26, which facilitates use of the fixation mechanisms 24 with the interbody device 22. The interbody device 22 is preferably formed of a PEEK material (e.g., with titanium X-ray markers), while the face plate 26 is preferably formed of titanium alloy, or Nitinol.

Figure 2:
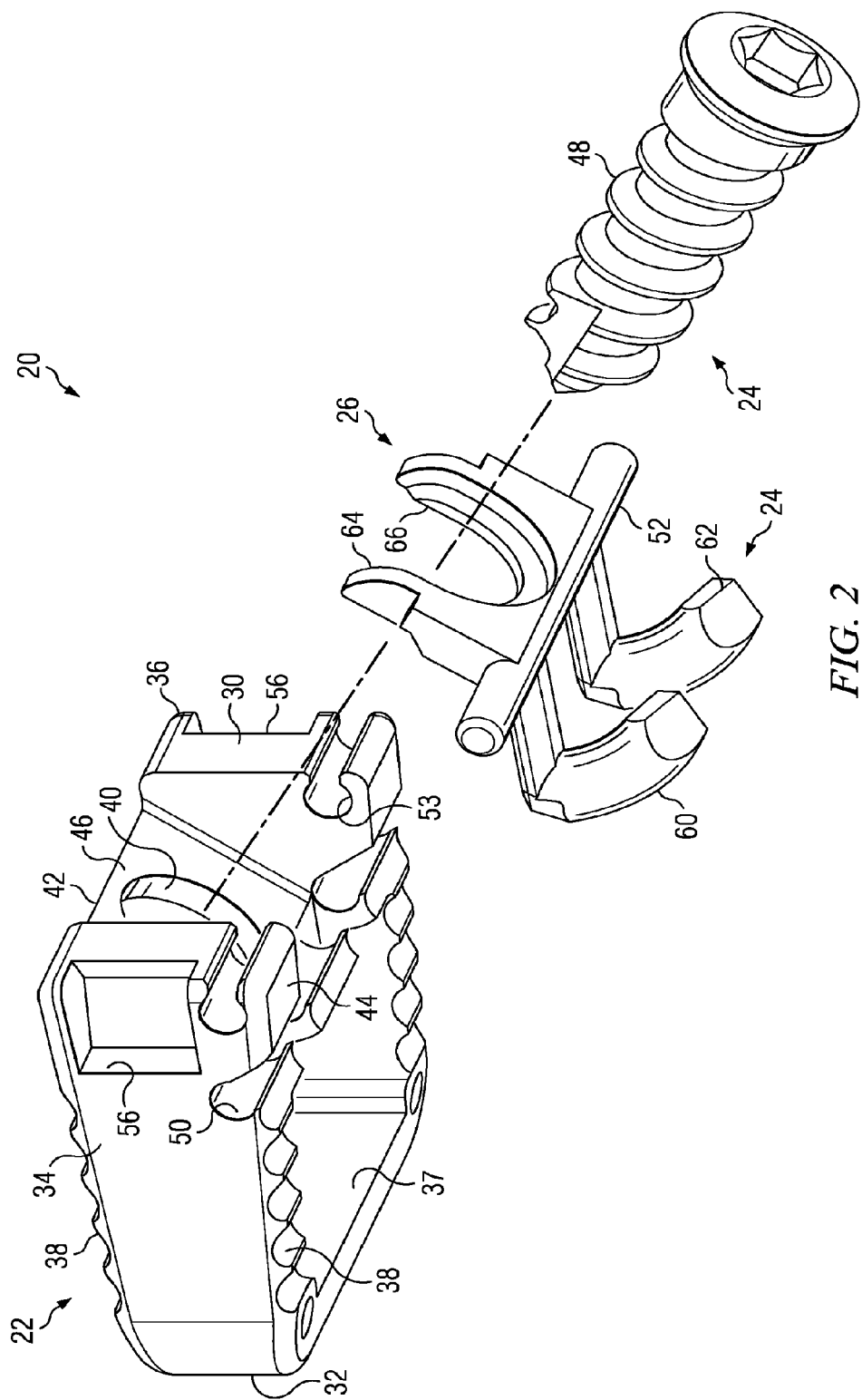
FIG. 2 illustrates an exploded view of an intervertebral disc prosthesis according to one embodiment of the present disclosure.
Figure 3:
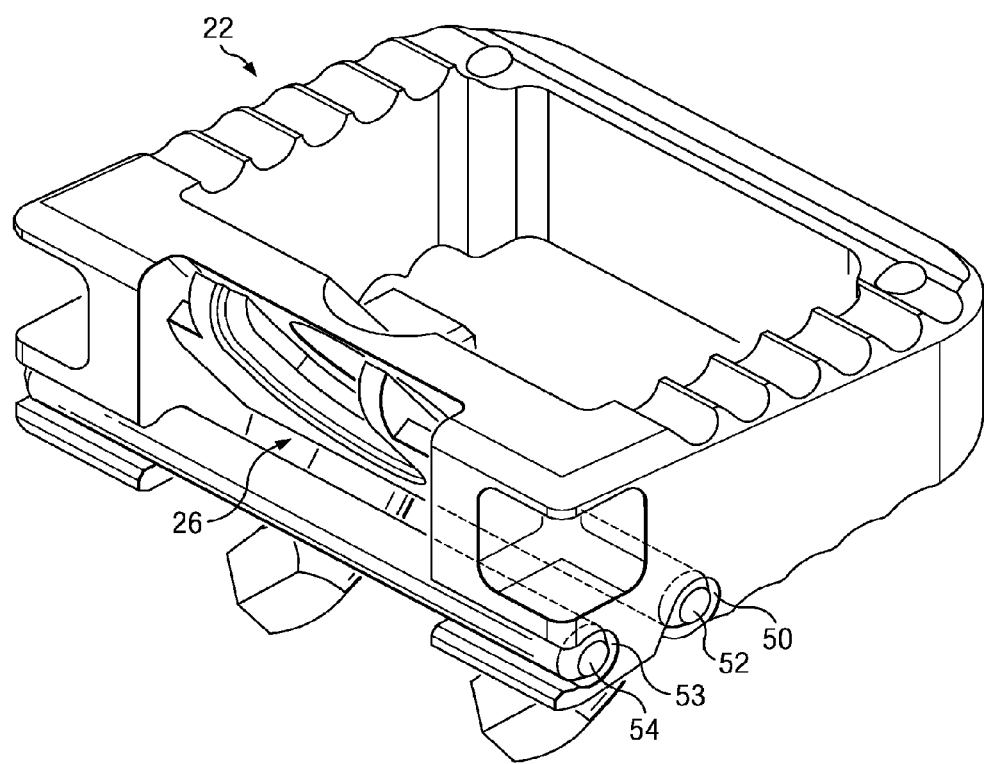
FIG. 3 illustrates a top perspective view of an interbody device and face plate of the intervertebral disc prosthesis of FIG. 2

The interbody device 22 may be sized and shaped to correspond to the anatomical contour of an intervertebral disc space (18 in FIG. 1B) created by the removal of an organic intervertebral disc (16 in FIG. 1B). Referring to FIG. 2, the interbody device 22 is generally quadrilateral in shape and includes an anterior portion 30, which is connected to a posterior portion 32 via two side portions 34, 36. Such portions cooperate to define a central opening 37 through the interbody device 22, which allows for passage of the fixation mechanisms 24 (and packing of bone graft material) as will be further described. Preferably, the side portions 34, 36 are slightly sloped in the anterior-posterior direction, thus resulting in a slightly smaller width at the posterior portion 32 of the interbody device 22 relative to the anterior portion 30. However, in other embodiments, the side portions 34, 36 may be relatively flat in the anterior-posterior direction, thus resulting in substantially the same width at the posterior portion 32 relative to the anterior portion 30. The top and bottom surfaces of the side portions 34, 36 may include ribs 38 or some other undulating surface to provide increased gripping of the adjacent vertebral endplates.

The anterior portion 30 of the interbody device 22 includes a face portion 40, which is preferably a recessed portion that extends in an oblique manner from a top side 42 of the interbody device 22 towards a bottom side 44 of the interbody device. The face portion 40 matches the contour of the face plate 26 and includes an aperture 46 defined therethough to receive a locking mechanism. In some embodiments, the fixation mechanism may be a threaded screw 48. Of course, other fixation mechanisms may be used, such as pins and the like.

The interbody device 22 further includes a slot 50 formed in the bottom side 44 to receive a rod member 52 of the face plate 26. An additional slot 53 may be formed in the anterior portion 30 of the interbody device 22 to receive a retaining member 54 (FIG. 3) to thereby protect against dislodgement of the face plate 26 from the interbody device when assembled. Still further, grooves 56 may be formed in the anterior portion 30 to permit handling of the interbody device 22 during insertion procedures. For example, various tools may be used to grip the interbody device at the grooves 56 to facilitate insertion of the disc prosthesis 20 into the disc space (18 in FIG. 1B) as will be further described.

Still referring to FIG. 2, in one embodiment, one of the fixation mechanisms 24 associated with the interbody device 22 may be formed unitarily with the face plate 26 and include a pair of tusks 60, which are adapted to engage an adjacent vertebral end plate (e.g., an endplate of the vertebrae 12 in FIG. 1A). To facilitate such engagement, the tusks 60 include sharpened endpoints 62, often referred to in the industry as trocars, to impact the adjacent end plate. It is to be appreciated that although two tusks 60 are illustrated, one or several tusks may be employed depending on the desired amount of engagement. Of course, other types of fixation mechanisms, other than the depicted tusks, may be utilized so long as a mechanism is provided for engaging and fixing the interbody device 22 to the vertebral endplates.

As discussed above, the face plate 26 is shaped to generally match the contour of the face portion 40 of the interbody device 22. Accordingly, the face plate 26 preferably includes a U-shaped portion 64, which is adapted to seat against the face portion 40. A slot 66 defined by the U-shaped portion 64 of the face plate 26 matches the aperture 46 defined in the face portion 40 of the interbody device 22 such that these openings are aligned when the face plate is seated against the interbody device. In other embodiments, the face plate 26 may include an aperture formed therethrough which corresponds to the aperture 46 of the face portion 40.

The face plate 26 further includes the laterally extending rod member 52, which is shaped to fit into the slot 50 formed in the interbody device 22. The rod member 52 may be unitarily formed with the face plate 26, or it may comprise a detachable member.

Figure 4:
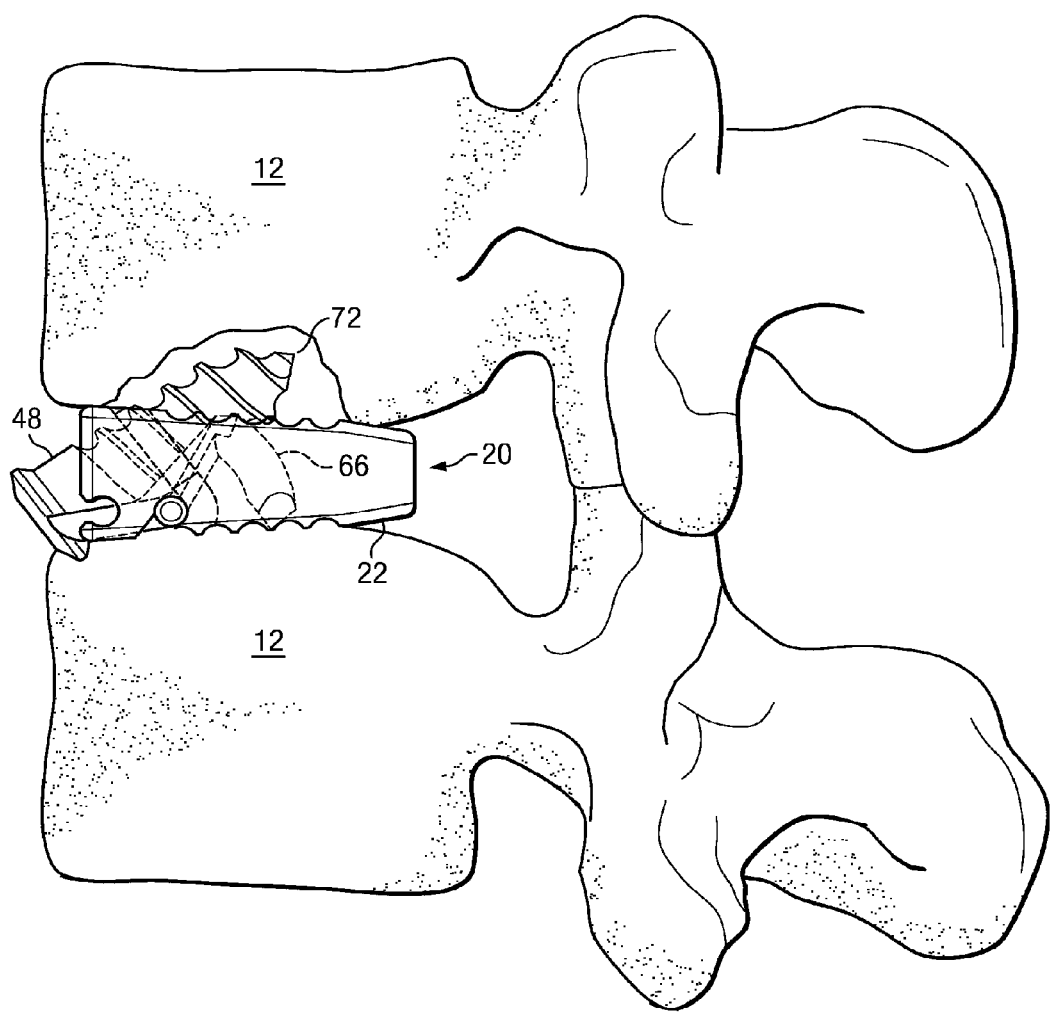
FIG. 4 illustrates a first position of the intervertebral disc prosthesis of FIG. 2 during an insertion procedure.

Referring to FIG. 4, in an initial position, the face plate 26 is situated with the interbody device 22 in such a way that the tusks 66 are substantially positioned within the central opening 37 defined by the interbody device. However, the rod member 52 provides a pivot point about which the face plate 26 may rotate to achieve a desired inserted position of the tusks 66 as will be described.

In one embodiment, an additional fixation mechanism 24 may take the form of the threaded screw 48, which cooperates with the interbody device 22 and face plate 26 to provide an additional point of engagement with the surrounding vertebral endplates (e.g., an opposing endplate relative to the endplate receiving the tusks 66). The screw 48 includes a sharpened end point 72, which is adapted to engage an intervertebral end plate to thereby secure the disc prosthesis 20 in the disc space as will be described. Although the threaded screw 48 represents a preferred embodiment, other fixation mechanisms may be used such as pins, or other elongated devices.

In operation, and after the removal of an organic intervertebral disc, a surgeon may implant the intervertebral disc prosthesis 20 into the disc space (18 in FIG. 1B). In some embodiments, the surgeon may use a tool (an example of which is discussed with reference to FIG. 6) to grip the interbody device 22 at the grooves 56 and position the device adjacent the disc space 18. The interbody device 22 (with associated face plate 26 and tusks 60) may then be impacted into the disc space using conventional impaction techniques. The ribs 38 formed on the interbody device 22 may facilitate initial securing of the interbody device within the disc space 18. Once the interbody device 22 is impacted and initially secured in the disc space 18, the screw 48 may then be inserted through the aligned aperture 46/slot 66 of the interbody device 22 and face plate 26, respectively.

Figure 5:
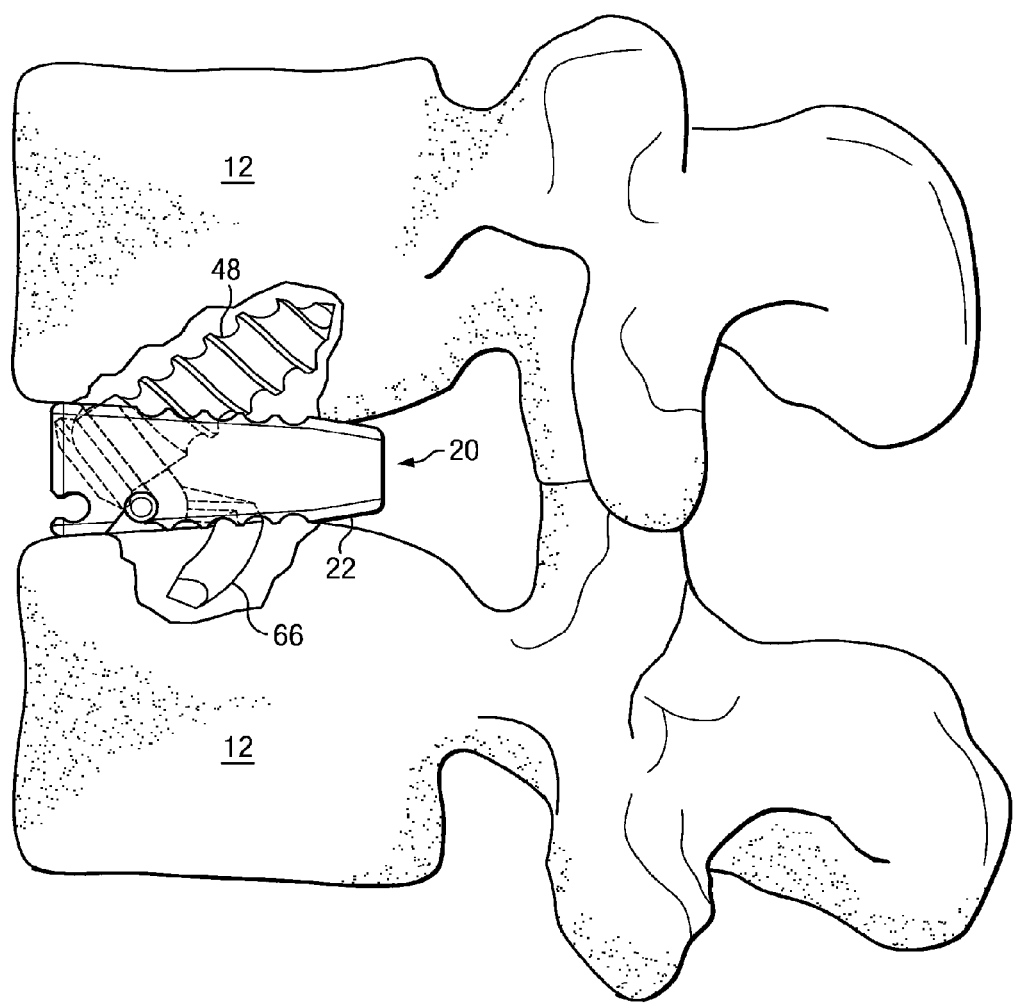
FIG. 5 illustrates a second, engaged position of the intervertebral disc prosthesis of FIG. 2.

Given the oblique face portion 40 of the interbody device 22 together with the matching contour of the face plate 26, insertion of the screw 48 results in the screw extending in a oblique manner relative to the top and bottom sides 42, 44 of the interbody device. The screw may then be engaged with a screwdriver to facilitate insertion of the screw into the adjacent intervertebral endplate, thus providing an attachment point of the disc prosthesis 20 with the spinal segment. Continued insertion of the screw 48 causes the head of the screw to engage the face plate 26 and urge the face plate against the face portion 40. Such force causes the face plate 26 to rotate about the rod member 52, which causes rotation of the tusks 66 into the adjacent vertebral endplate (in this embodiment, the endplate opposing the endplate receiving the screw 48). As the screw is further inserted into its associated endplate, the tusks 66 are accordingly further pushed into its associated endplate until the desired level of dual fixation is achieved, an example of which is shown in FIG. 5.

Figure 6A:
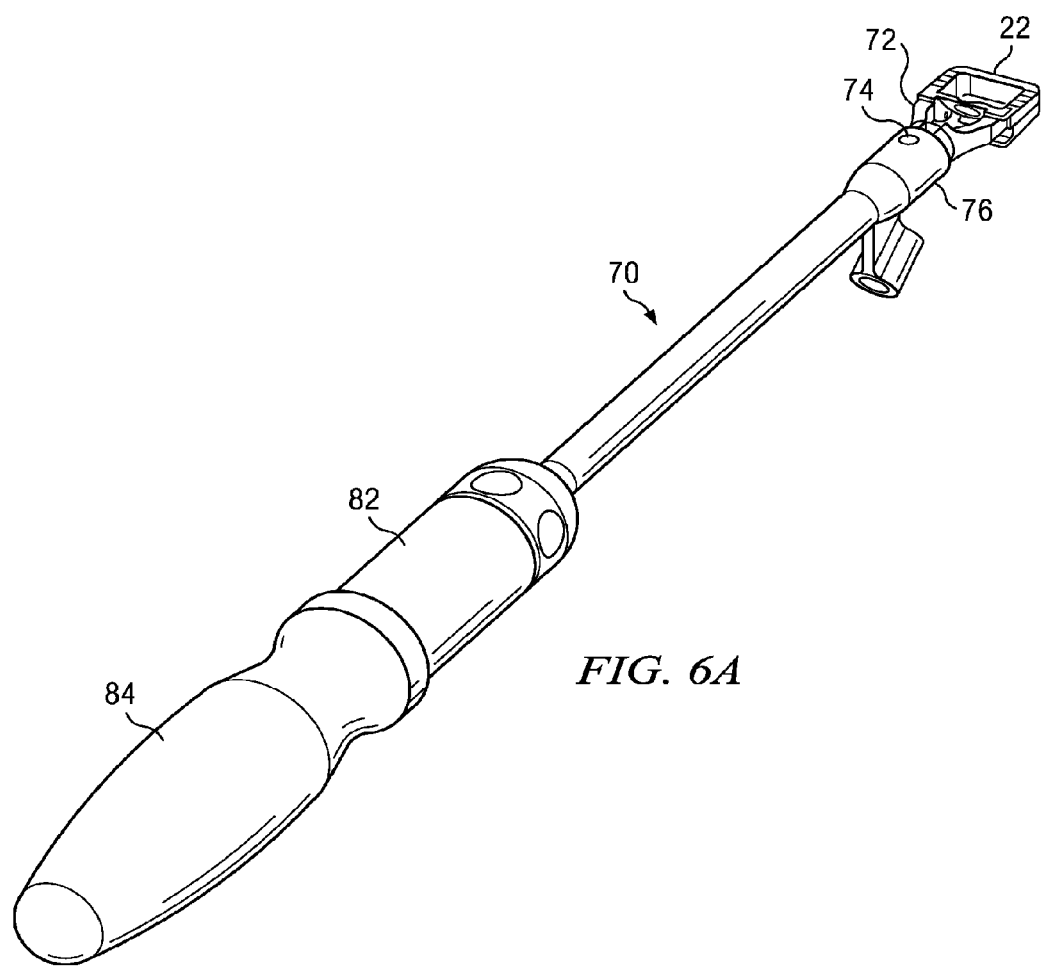
FIG. 6A illustrates an exemplary tool for inserting the intervertebral disc prosthesis of the present disclosure into an intervertebral disc space.
Figure 6B:
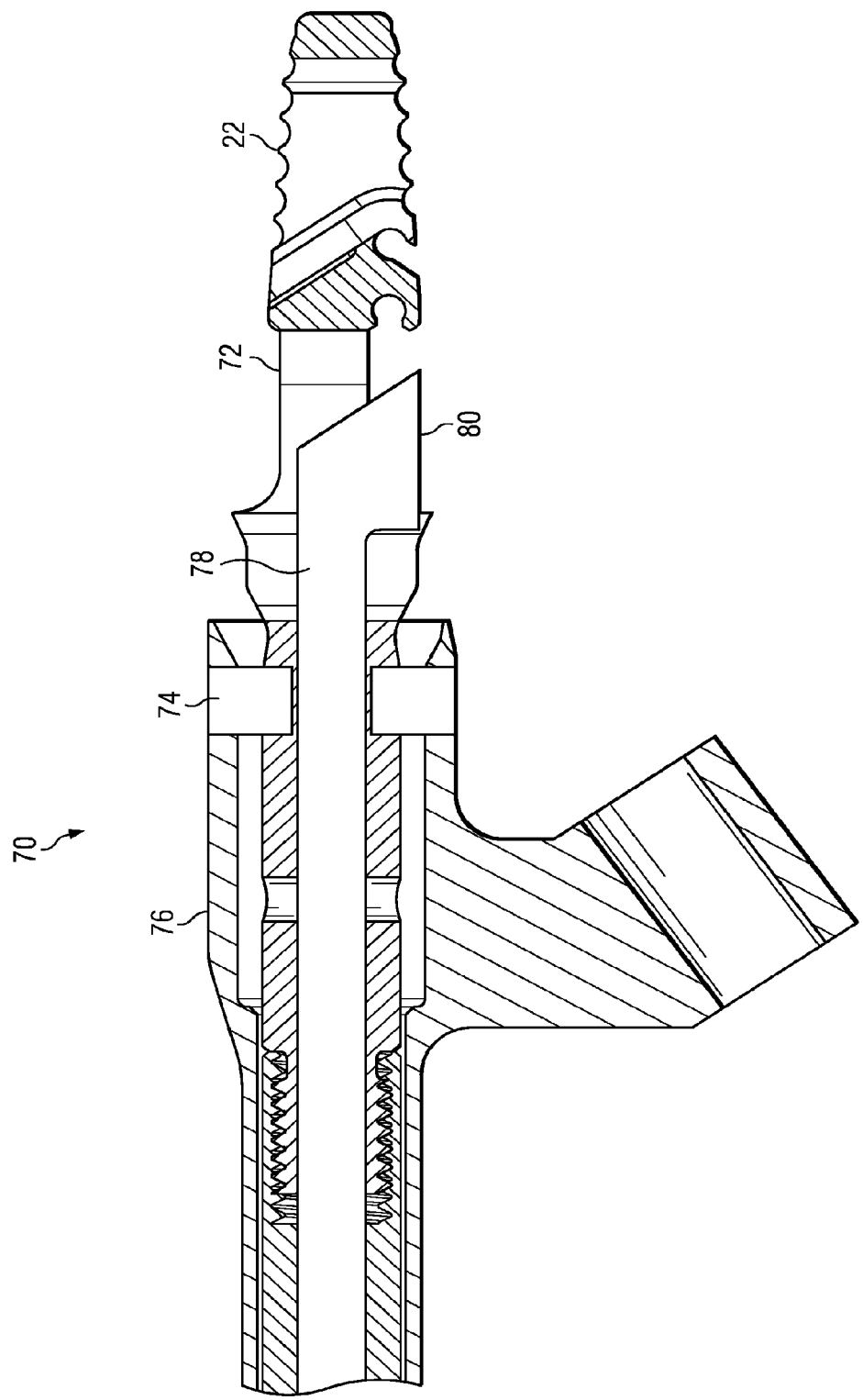
FIG. 6B illustrates a distal portion of the tool of FIG. 6A in section.

A tool 70 for inserting the disc prosthesis 20 into the intervertebral disc space 18 is illustrated in FIGS. 6A-B. The tool 70 includes a distal gripping member 72, which is adapted to grip the interbody device 22 for insertion into the intervertebral disc space 18. The tool 70 further includes a pin 74 connected to a sleeve 76. In practice, pulling of the sleeve 76 pushes pin 74 into a channel formed in the gripping member 72, thus spreading gripping member apart. Then, by pushing the sleeve 76 forward, the gripping member 72 closes and thus grips the interbody device 22 for insertion.

The tool 70 further includes an internal shaft 78 having a wedge-shaped member 80 disposed at a distal end thereof. In practice, once the gripping member 72 grips the interbody device 22, the shaft 78 may be actuated forward to urge the wedge-shaped member 80 against the interbody device 22 and into the intervertebral disc space. Of course, the member 80 may take on shapes other than a wedge-shape, so long as it is capable of being urged against the interbody device 22 to thereby insert the interbody device into the disc space. The shaft 78 may be actuated by rotating a knob 82 disposed adjacent to a handle 84 of the tool 70.

Figure 7:
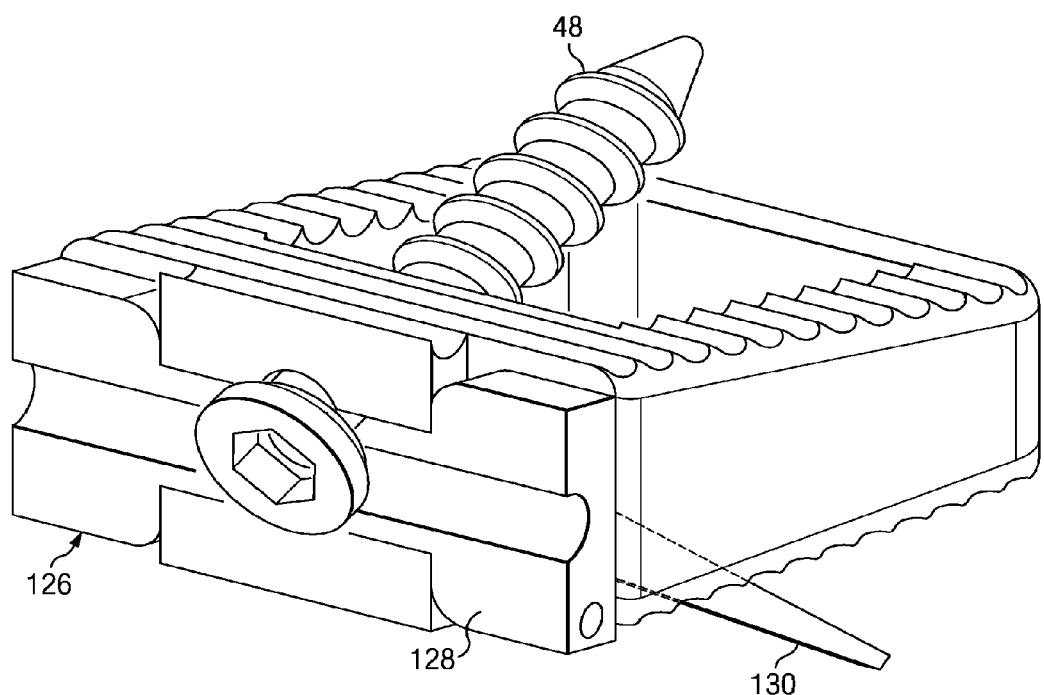
FIG. 7 illustrates an alternative intervertebral disc prosthesis according to another embodiment of the present disclosure.

Having described a preferred embodiment of the intervertebral disc prosthesis 20 and its associated method of insertion, it is to be appreciated that the disc prosthesis may take on alternative configurations without departing from the spirit or scope of the present disclosure. For example, referring to FIG. 7, an alternative face plate 126 may include a face portion 128 and a pair of staples 130 (or keels, one of which is shown in FIG. 7) extending at a generally oblique angle from the face portion. Much like the tusk embodiment, insertion of the screw 48 will cause deformation of the face plate about a rod member (not shown) and thus insertion of the staples 130 into the adjacent vertebral endplate.

The teachings of the present disclosure are advantageous in several respects. For example, the insertion procedure described herein involves single step fixation via insertion of a single screw or insertion instrument to fold up the face plate. Such a simplified procedure reduces the inherent risks associated with operating in such a sensitive region of the human anatomy. Furthermore, single step fixation achieves dual-point fixation as screw insertion controls both cephalad fixation (via the screw 48) as well as caudal fixation (via the tusks 66 or staples 130, which are activated by pivoting of the face plate 26, 126). Still further, the positioning of the screw 48 relative to the interbody device 22 facilitates repeatable trajectory, thus allowing surgeons to plan for required exposure. Moreover, the dual fixation design of the intervertebral disc prosthesis 20 offers alternative manners of insertion as the disc prosthesis may also be used in an inverted manner (i.e., the screw 48 may be utilized for caudal fixation and the tusks 66 for cephalad fixation).

While various embodiments of an intervertebral disc prosthesis and related methods of implanting such devices, have been described above, it should be understood that they have been presented by way of example only, and not limitation. Thus, the breadth and scope of the present disclosure should not be limited by any of the above-described exemplary embodiments, but should be defined only in accordance with the following claims and their equivalents. Moreover, the above advantages and features are provided in described embodiments, but shall not limit the application of the claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," the claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in the claims found herein. Furthermore, any reference in this disclosure to "invention" in the singular should not be used to argue that there is only a single point of novelty claimed in this disclosure. Multiple inventions may be set forth according to the limitations of the multiple claims associated with this disclosure, and the claims accordingly define the invention(s), and their equivalents, that are protected thereby. In all instances, the scope of the claims shall be considered on their own merits in light of the specification, but should not be constrained by the headings set forth herein.

What is claimed is:

1. A method of using an intervertebral disc prosthesis, comprising:
   providing an intervertebral disc prosthesis, the prosthesis comprising an interbody device, a face plate having one or more fixation mechanisms integrally connected therewith, and one or more additional fixation mechanisms;
   connecting the face plate to the interbody device such that the one or more fixation mechanisms are substantially disposed within a central opening defined in the interbody device;
   inserting the interbody device and face plate into an intervertebral disc space; and
   inserting the one or more additional fixation mechanisms through the face plate and interbody device and into a first vertebral endplate;
   whereby inserting the one or more additional fixation mechanisms urges the face plate against the interbody device, thereby causing the one or more fixation mechanisms to rotate into a second vertebral endplate opposing the first vertebral endplate.

2. A method according to claim 1, wherein the one or more additional fixation mechanisms comprises a screw, the method comprising inserting the screw through the face plate and interbody device and into the first vertebral endplate.

3. A method according to claim 1, wherein the one or more fixation mechanisms comprises a pair of tusks integrally connected to the face plate, whereby urging of the face plate against the interbody device causes the tusks to rotate into the second vertebral endplate.

4. A method according to claim 1, wherein the one or more fixation mechanisms comprises a pair of staples integrally connected to the face plate, whereby urging of the face plate against the interbody device causes the staples to rotate into the second vertebral endplate.

5. A method according to claim 1, wherein the interbody device includes a slot formed therein, the method further comprising disposing a retaining member in the slot to thereby prevent the face plate from dislodging from the interbody device.

* * * * *